US00PP20793P2

(12) United States Plant Patent
Fleischle

(10) Patent No.: US PP20,793 P2
(45) Date of Patent: Feb. 23, 2010

(54) ***STREPTOCARPUS* PLANT NAMED 'ROULETTE AZUR'**

(50) Latin Name: *Streptocarpus×hybridus voss*
Varietal Denomination: Roulette Azur

(75) Inventor: Achim Fleischle, Vaihingen/Enz (DE)

(73) Assignee: Fleischle Gartenbau GbR, Vaihingen/Enz (DE)

( * ) Notice: Subject to any disclaimer, the term of this patent is extended or adjusted under 35 U.S.C. 154(b) by 0 days.

(21) Appl. No.: 12/150,554

(22) Filed: Apr. 29, 2008

(51) Int. Cl.
*A01H 5/00* (2006.01)

(52) U.S. Cl. ..... Plt./333

(58) Field of Classification Search ..... Plt./333
See application file for complete search history.

*Primary Examiner*—June Hwu
(74) *Attorney, Agent, or Firm*—Mark P. Bourgeois

(57) ABSTRACT

A new cultivar of *Streptocarpus* plant named 'Roulette Azur' that is characterized by a large quantity of white flowers with violet margins primarily on the lower three petals, short leaves and short pedicels.

1 Drawing Sheet

Botanical classification: *Streptocarpus×hybridus Voss.*
Variety denomination: 'Roulette Azur'.

BACKGROUND OF THE INVENTION

The present invention relates to a new and distinct cultivar of *Streptocarpus* plant botanically known as *Streptocarpus* and hereinafter referred to by the cultivar name 'Roulette Azur'.

'Roulette Azur' is a hybrid that originated from a crossing in the June of 2004 of the female or seed parent *Streptocarpus* cultivar named 'Roulette Cherry' and the male or pollen parent an unnamed proprietary *Streptocarpus* cultivar (not patented). The resulting seeds were subsequently planted and grown. The cultivar 'Roulette Azur' was selected by the inventor in April of 2005 as a single plant within the progeny of the stated cross in Vaihingen/Enz, Germany.

Asexual reproduction of the new cultivar 'Roulette Azur' first occurred by leaf cuttings in July of 2005 in Vaihingen/Enz, Germany. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Streptocarpus* cultivar 'Roulette Azur'. These traits in combination distinguish 'Roulette Azur' as a new and distinct cultivar apart from other existing known varieties of *Streptocarpus*.

1. *Streptocarpus* 'Roulette Azur' exhibits a large quantity of flowers.
2. *Streptocarpus* 'Roulette Azur' exhibits white flowers with violet margins primarily on the lower three petals.
3. *Streptocarpus* 'Roulette Azur' exhibits short leaves.
4. *Streptocarpus* 'Roulette Azur' exhibits short pedicels.

The closest comparison cultivar is *Streptocarpus* 'Spirit' (U.S. Plant patent application No. 12/150,575).

'Roulette Azur' is distinguishable from 'Spirit' by the following characteristics:

1. 'Roulette Azur' has flowers with an undulating petal rim.

2. 'Roulette Azur' has white flowers with violet margins primarily on the lower three petals. The flowers of 'Spirit' are light blue with dark violet veins.
3. 'Roulette Azur' has light green pedicels. The pedicels of 'Spirit' are dark purple-green.
4. 'Roulette Azur' exhibits flowers that are rounded. The flowers of 'Spirit' are more angular.

'Roulette Azur' is distinguishable from the female or seed parent 'Roulette Cherry' (U.S. Plant patent application No. 12/150,589) by the following characteristics:

1. 'Roulette Azur' has white flowers with violet margins primarily on the lower three petals. The flowers of 'Roulette Cherry' are white with red outer lobes.
2. 'Roulette Azur' has smaller flowers.
3. 'Roulette Azur' has shorter leaves.
4. 'Roulette Azur' has shorter pedicels.

'Roulette Azur' is distinguishable from the unnamed male or pollen parent by the following characteristics:

1. 'Roulette Azur' has white flowers with violet margins primarily on the lower three petals. The flowers of the pollen parent are white.
2. 'Roulette Azur' has larger flowers.

BRIEF DESCRIPTION OF THE DRAWING

The accompanying photograph illustrates the distinguishing traits of *Streptocarpus* 'Roulette Azur'. The plant in the photograph shows an overall view of a 10 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Streptocarpus* cultivar named 'Roulette Azur'. Data was collected in Vaihingen/Enz, Germany from 10 week old glass greenhouse grown plants in 12 cm. diameter containers. The time of year was Winter and the temperature range was 20-22 degrees Centigrade during the day and 18-22 degrees Centigrade at night. The light level was 2000 to 3000 Lux. No photoperiodic treatments or growth retardants were used. Color determinations are in accordance with The Royal Horticultural Society Colour Chart 2007 edition, except where general color terms of ordinary dictionary significance are used. The growing requirements are similar to the species. 'Roulette Azur' has not been tested under all possible conditions and phenotypic differences may be observed with variations in environmental, climatic, and cultural conditions, however, without any variance in genotype.

Botanical classification: *Streptocarpus* 'Roulette Azur'.

Use: Indoor plant or ornamental perennial in warmer climates.

Parentage: 'Roulette Azur' is a hybrid of the female or seed parent *Streptocarpus* 'Roulette Cherry' and the male or pollen parent an unnamed proprietary *Streptocarpus* cultivar.

Vigor: Moderate.

Growth habit: Ground hugging, clump forming.

Plant shape: Rounded, clump forming plant with upright leaves.

Suitable container size: 12 cm. pots.

Height: 15 cm. in height.

Width: 26 cm. in width.

Low temperature tolerance: 8° Centigrade.

High temperature tolerance: 30° Centigrade.

Propagation: Leaf cuttings.

Time to initiate roots in summer: 25 days to initiate roots at 24° Centigrade.

Time to initiate roots in winter: 21 days to initiate roots at 22° Centigrade.

Time to produce a rooted cutting or liner in summer: 135 days at 24° Centigrade.

Time to produce a rooted cutting or liner in winter: 125 days at 22° Centigrade.

Crop time: Approximately 8 to 10 weeks.

Root system: Fibrous.

Stem: No stems, Leaves grow directly from base, Average 13 clumps.

Foliage:

*Texture.*—Glossy.

*Leaf arrangement.*—In whorls.

*Compound or single.*—Single.

*Leaf shape.*—Obolanceolate.

*Leaf apex.*—Obtuse.

*Leaf base.*—Attenuate.

*Leaf length.*—22.0 cm. in length.

*Leaf width.*—7.0 cm. in width.

*Pubescence.*—Upper side coarse and dense, lower side puberulent.

*Leaf margin.*—Crenulate, undulate.

*Young leaf color* (*lower surface*).—138C.

*Young leaf color* (*upper surface*).—N137A.

*Mature leaf color* (*lower surface*).—138C.

*Mature leaf color* (*upper surface*).—N137A.

*Vein color* (*under surface*).—138D.

*Vein color* (*upper surface*).—137D.

*Venation pattern.*—Strong midrib with alternating lateral veins.

*Leaf attachment.*—Petiolate.

*Petiole dimensions.*—4 cm. in length, and 60 mm. in diameter.

*Petiole surface texture.*—Slight pubescent.

*Petiole color.*—138C.

Flower:

*Inflorescence arrangement.*—Raceme.

*Flowering habit.*—Continuous.

*Quantity of flowers per inflorescence.*—Average 5.

*Inflorescence dimensions.*—13 cm. in height and 8 cm. in width.

*Flower type.*—Zygomorph with five petals fused to a conical throat ending in a flaring five lobed corolla disk.

*Quantity of flowers per lateral stem.*—Average 5.

*Quantity of flower buds per lateral stem.*—4-5.

*Quantity of flowers and buds per plant.*—At any given time up to 20.

*Natural flowering season.*—All year.

*Fragrance.*—None.

*Rate of flower opening.*—Within two weeks of visible raceme.

*Flower bud length.*—4 cm.

*Flower bud diameter.*—1.5 cm.

*Flower bud shape.*—Elongated, club-shaped.

*Bud color.*—145 D.

*Rate of bud opening.*—2 days.

*Flower aspect.*—Funnel drooping, corolla disk outward-facing.

*Flower shape.*—Trumpet-shaped with flat, flaring corolla disk.

*Flower dimensions.*—5 cm in diameter and 5 cm in depth.

*Flower longevity.*—4-5 days.

*Petal texture.*—Velvety, soft.

*Number of petals.*—5.

*Fused or unfused.*—Fused.

*Petal arrangement.*—Evenly spaced, radiating, zygomorphic.

*Petal shape.*—Orbicular.

*Petal margin.*—Crenate.

*Petal apex.*—Obtuse.

*Petal length.*—14-15 mm. before fused to corolla.

*Petal width.*—1.5 cm.

*Petal color when opening* (*upper side*).—NN155C, lower petals with margins of N87A to N88A.

*Petal color when opening* (*under side*).—NN155C, lower petals with margins of N87A to N88A.

*Petal color fully opened* (*upper side*).—NN155C, lower petals with margins of N87A to N88A.

*Petal color fully opened* (*under side*).—NN155C, lower petals with margins of N87A to N88A.

*Petal color fading to.*—Not fading.

*Throat.*—Tubular, 32 mm. in length, 6 mm. in diameter near base, 9 mm. in diameter at flare, inner color NN155D, outer color NN155B.

*Self-cleaning or persistent.*—Self-cleaning.

Sepals:

*Number of sepals.*—5.

*Sepal shape.*—Linear.

*Sepal margin.*—Entire.

*Sepal apex.*—Acuminate.

*Sepal base.*—Fused, linear.

*Sepal dimensions.*—5 mm. in length and 2 mm. in width.

*Young sepal color* (*upper side*).—145A.

*Young sepal color* (*under side*).—145A.

*Mature sepal color* (*upper side*).—145A.

*Mature sepal color* (*under side*).—145A.

Calyx:

*Calyx shape.*—Elongated corona.

*Calyx dimensions.*—7 mm. in length and 3 mm. in diameter.

Peduncle:

*Peduncle length.*—1.5 - 2 cm.

*Peduncle diameter.*—2 mm.

*Peduncle strength.*—Moderate.

*Peduncle surface texture.*—Slight pubescent.

*Peduncle color.*—145A.

Pedicels:

*Pedicel length.*—15 cm.

*Pedicel diameter.*—3 mm.

*Pedicel strength.*—Moderate.

*Pedicel surface texture.*—Slight pubescent.

*Pedicel color.*—145A.

Reproduction organs:

*Stamen number.*—Two.

*Anther shape.*—Fused.

*Anther color.*—162B.

*Amount of pollen.*—Low.

*Pollen color.*—162B.

*Pistil number.*—One.

*Pistil length.*—3 cm. in length.

*Stigma shape.*—Deltoid, bifurcate.

*Stigma color.*—145C.

*Style length.*—12 mm.

*Style color.*—NN155C.

*Ovary color.*—145C.

Fruit:

*Fruit dimensions.*—2.5 cm. in length and 0.5 cm. in diameter.

*Fruit color.*—165A.

Seed:

*Seed dimensions.*—0.3 mm. in length and 0.2 mm. in diameter.

*Seed color.*—165D.

*Quantity of seeds.*—50-60.

Disease resistance: Susceptible to *Streptocarpus* flower mottle virus.

The invention claimed is:

1. A new and distinct variety of *Streptocarpus* plant named 'Roulette Azur' as described and illustrated.

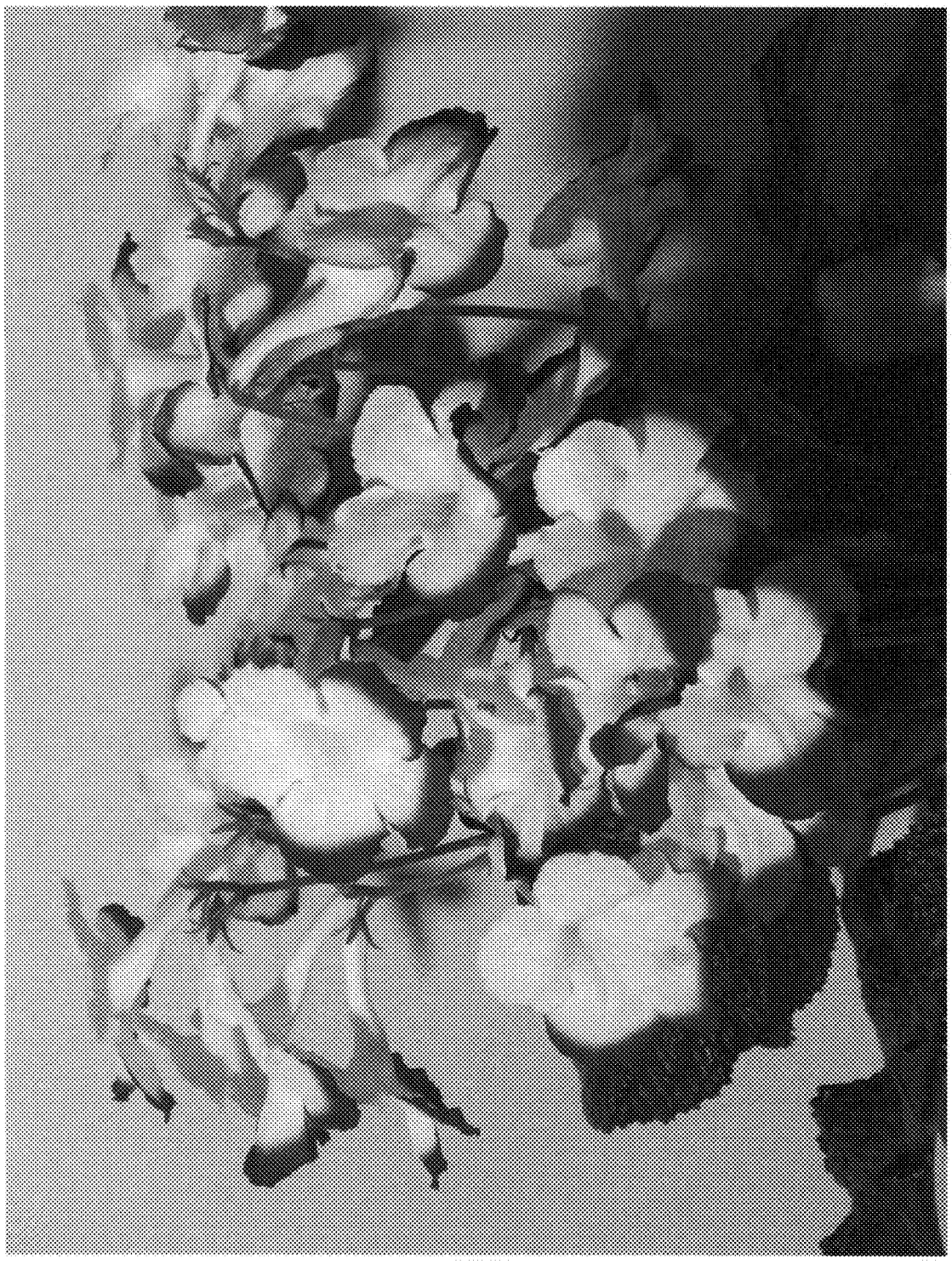

* * * * *